United States Patent
Kritzman et al.

(10) Patent No.: US 6,719,691 B2
(45) Date of Patent: Apr. 13, 2004

(54) METHOD, DEVICE AND KIT FOR OBTAINING BIOLOGICAL SAMPLES

(75) Inventors: Amnon Kritzman, Zichron Yaakov (IL); Yael Bechar, Ein Ayala (IL); Hadar Kessary Shoham, Zichron Yaakov (IL)

(73) Assignee: Common Sense Ltd., Caesarea (IL)

( * ) Notice: Subject to any disclaimer, the term of this patent is extended or adjusted under 35 U.S.C. 154(b) by 217 days.

(21) Appl. No.: 09/912,497

(22) Filed: Jul. 26, 2001

(65) Prior Publication Data

US 2003/0023188 A1 Jan. 30, 2003

(51) Int. Cl.[7] ............ A61B 5/00; B65D 71/00; B65D 85/38; G01N 31/22; A61M 35/00
(52) U.S. Cl. ............ 600/362; 206/569; 206/305; 422/58; 604/1
(58) Field of Search ............ 600/309, 362; 604/1; 206/569, 305; 422/56, 58, 61; 435/30

(56) References Cited

U.S. PATENT DOCUMENTS

| | | | |
|---|---|---|---|
| RE24,666 E | 7/1959 | Draghi | 128/285 |
| 2,929,379 A | 3/1960 | Poulsen | 128/290 |
| 3,731,685 A | 5/1973 | Eidus | 128/284 |
| 3,850,160 A | 11/1974 | Denson | 128/2 B |
| 3,918,433 A | 11/1975 | Fuisz | 128/2 F |
| 3,934,575 A | 1/1976 | Bucalo | 128/2 W |
| 4,072,150 A | 2/1978 | Glassman | 128/284 |
| 4,114,621 A | 9/1978 | Mims, Jr. | 128/288 |
| 4,207,394 A * | 6/1980 | Aldridge et al. | 435/34 |
| 4,353,868 A * | 10/1982 | Joslin et al. | 422/101 |
| 4,444,193 A | 4/1984 | Fogt et al. | 128/632 |
| 4,605,404 A | 8/1986 | Sneider | 604/385 |
| 4,789,629 A | 12/1988 | Baker et al. | 435/7 |
| 4,806,408 A | 2/1989 | Pierre et al. | 428/76 |
| 4,808,379 A | 2/1989 | Wardlaw et al. | 422/56 |
| 4,978,504 A * | 12/1990 | Nason | 422/61 |
| 5,088,502 A | 2/1992 | Miller | 128/759 |
| 5,119,828 A | 6/1992 | Miller | 128/760 |
| 5,231,992 A | 8/1993 | Leon | 128/759 |
| 5,429,631 A | 7/1995 | Grenier | 604/385.1 |
| 5,432,097 A | 7/1995 | Yourno | 436/175 |
| 5,676,144 A | 10/1997 | Schoendorfer | 128/632 |
| 5,876,389 A | 3/1999 | Bouchard et al. | 604/385.1 |
| 6,126,597 A | 10/2000 | Smith et al. | 600/362 |
| 6,149,590 A | 11/2000 | Smith et al. | 600/367 |
| 6,426,227 B1 * | 7/2002 | Kritzman et al. | 436/43 |
| 6,627,394 B2 * | 9/2003 | Kritzman et al. | 435/4 |

FOREIGN PATENT DOCUMENTS

| | | | |
|---|---|---|---|
| DE | 38 10473 | 10/1989 | 604/361 |
| EP | 0 312 293 * | 4/1989 | A61B/5/00 |
| FR | 2 599 500 | 6/1968 | |
| FR | 2 399 231 | 3/1979 | |
| GB | 520576 | 4/1990 | 604/385.1 |
| WO | 91/19471 | 12/1991 | 604/361 |
| WO | 94/10958 | 5/1994 | 604/361 |

* cited by examiner

*Primary Examiner*—Weilun Lo
*Assistant Examiner*—Michael G. Bogart
(74) *Attorney, Agent, or Firm*—Winston & Strawn LLP

(57) ABSTRACT

A kit for generating a biological sample from a discharge emitted from a portion of a body includes an absorbent pad for deploying adjacent to the portion of the body and a portable device for preserving and/or pre-processing the sample. The pad includes a sampling membrane configured to retain at least one biological material. The portable device has a housing formed from a base portion and lid portion which together define a sealable sample chamber for receiving the sampling membrane. An injector device is configured to be activated by closing of the lid portion to inject sample extracting solution into the sample chamber.

39 Claims, 19 Drawing Sheets

METHOD, DEVICE AND KIT FOR OBTAINING BIOLOGICAL SAMPLES

FIELD AND BACKGROUND OF THE INVENTION

The present invention relates to medical sampling techniques and, in particular, it concerns a kit and corresponding method for obtaining a biological sample.

Many medical conditions may be diagnosed and/or monitored by performing various tests of samples of discharges. For example, analysis of vaginal discharges by various well documented tests is effective for diagnosis of sexually transmitted and other medical conditions including, but not limited to, infection by candida or chlamydia, trichomoniasis and bacterial vaginosis (BV). Tests of this type are typically performed on a sample taken during a clinical examination by a health care professional.

It has been proposed to perform tests of this type on discharges collected by an absorbent pad or the like used by the patient. An example of a system for performing tests on such samples is disclosed in co-assigned PCT Patent Application Publication No. WO 01/16576.

Use of vaginal secretions contained in an absorbent pad offers a number of advantages when compared to other methods of obtaining samples of the same secretion. For example, most patients are capable of deploying and removing such a pad without aid. This means that a sample can be obtained without a gynecological examination. In addition, a patient suspecting an infection could bring or send a pad containing a sample to her doctor, making a subsequent appointment to receive the results and a prescription for treatment, if so required. This reduces the number of necessary medical appointments, an advantage for both patient and doctor. In some situations, for example patients living in remote areas or patients desiring anonymity for the initial stages of diagnosis, a pad containing a sample could be mailed to a medical center, with results and possibly a prescription being returned by phone or fax.

Despite these advantages, implementation of testing systems for samples absorbed in absorbent pads present a number of practical problems. A first problem is to ensure a sufficient quantity and concentration of the sample to allow testing to be effective. In order to extract any and all samples from the entire area of a pad, large quantities of solvents would be required so that the resultant sample would be greatly over-diluted. This issue is addressed by the aforementioned PCT publication WO 01/16576 by use of an optical system to identify the exact location of a sample within the pad. A more difficult problem is that of deterioration of the sample during transit. Since the sample is typically secreted onto the pad and subsequently forwarded to a remote location for analysis, the sample is usually not fresh when tested. The combined effects of drying and oxidation due to atmospheric exposure render the sample unsuitable for use in many tests and may reduce the reliability of many others.

There is therefore a need for a kit and corresponding method for obtaining a biological sample by use of an absorbent pad and in a manner which preserves the sample, or even enhances it, for subsequent analysis at a remote location.

SUMMARY OF THE INVENTION

The present invention is kit and corresponding method for obtaining a biological sample.

According to the teachings of the present invention there is provided, a method for obtaining a biological sample of a discharge emitted from a portion of a body, the method comprising: (a) deploying an absorbent pad adjacent to the portion of the body for a period of time; (b) inserting at least a part of the absorbent pad into a sample chamber of a portable device; (c) adding sample extraction solution into the sample chamber; (d) sealing the sample chamber; and (e) transporting the portable device to a remote location for processing of the biological sample dissolved within the sample extraction solution.

According to a further feature of the present invention, the part of the absorbent pad is a sampling membrane configured to retain at least one biological material, the absorbent pad being configured to facilitate removal of the sampling membrane.

According to a further feature of the present invention, the portable device further includes a receptacle within which the sample extraction solution is stored prior to adding into the sample chamber.

According to a further feature of the present invention, the receptacle is implemented as an injector device, and wherein the step of sealing automatically actuates the injector device to perform the step of adding the sample extraction solution into the sample chamber.

According to a further feature of the present invention, at least one sample pre-processing agent is supplied within the sample chamber. The sample pre-processing agent preferably includes at least one nutrient for maintaining activity of a pathogen and/or at least one antibiotic agent. Preferably, the sample pre-processing agent is supplied in a solid form.

According to a further feature of the present invention, a disposable heating device is deployed to maintain the biological sample at a temperature above ambient temperature for a given time period.

According to a further feature of the present invention, a disposable cooling device is deployed to maintain the biological sample at a temperature below ambient temperature for a given time period.

There is also provided according to the teachings of the present invention, a portable device for use in generating a biological sample from a discharge emitted from a portion of a body onto a sheet of material, the device comprising: (a) a housing including: (i) a base portion formed with a sample chamber for receiving the sheet of material, and (ii) a lid portion configured for sealingly closing the sample chamber; and (b) an injector device associated with the housing and pre-charged with a quantity of sample extracting solution, the injector device being configured to be activated by closing of the lid portion to inject at least part of the quantity of sample extracting solution into the sample chamber.

According to a further feature of the present invention, the sample chamber is configured to have an open area of at least about 20 cm$^2$ for insertion of the sheet of material.

According to a further feature of the present invention, the sample chamber is configured to have an enclosed volume when sealed of no more than about 5 cc, and preferably between 1.5 and 3 cc.

According to a further feature of the present invention, a major part of an enclosed volume of the sample chamber lies between a lower surface provided by the base portion and an upper surface provided by the lid portion, each of the lower and upper surfaces being formed with a plurality of projections projecting into the enclosed volume.

According to a further feature of the present invention, the lid portion is implemented with a top surface having a recessed portion, the injector device being deployed at least partially within the recessed portion.

According to a further feature of the present invention, the injector device is implemented as a syringe provided with a spring-loaded piston which is released by closing of the lid portion.

According to a further feature of the present invention, there is also provided a snap-lock configuration deployed to lock the lid portion closed against the base portion.

According to a further feature of the present invention, there is also provided a manually operable dispensing mechanism configured for dispensing a controlled quantity of liquid from the sample chamber.

According to a further feature of the present invention, the dispensing mechanism includes a finger-operable piston mechanism.

According to a further feature of the present invention, there is also provided a dropper aperture in fluid communication with the sample chamber for allowing release of liquid droplets from the sample chamber.

According to a further feature of the present invention, there is also provided (a) a removable sealing element deployed so as to seal the dropper aperture until immediately prior to dispensing of liquid from the sample chamber; and (b) a lock mechanism associated with the dispensing mechanism and configured to selectively prevent operation of the dispensing mechanism, the lock mechanism being mechanically linked to the removable sealing element so as to allow operation of the dispensing mechanism when the sealing element is removed.

There is also provided according to the teachings of the present invention, a kit for generating a biological sample from a discharge emitted from a portion of a body, the kit comprising: (a) an absorbent pad for deploying adjacent to the portion of the body, the pad including a sampling membrane configured to retain at least one biological material, the absorbent pad being configured to facilitate removal of the sampling membrane; and (b) a portable device including: (i) a housing having: (A) a base portion formed with a sample chamber for receiving the sampling membrane, and (B) a lid portion configured for sealingly closing the sample chamber; and (ii) an injector device associated with the housing and pre-charged with a quantity of sample extracting solution, the injector device being configured to be activated by closing of the lid portion to inject at least part of the quantity of sample extracting solution into the sample chamber.

According to a further feature of the present invention, the sampling membrane is configured for binding proteins.

According to a further feature of the present invention, the sampling membrane is associated with a frame located within, and withdrawable from, the absorbent pad.

According to a further feature of the present invention, the sampling membrane is associated with a handle configured to facilitate withdrawal of the sampling membrane from the absorbent pad.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a kit and corresponding method for obtaining a biological sample.

The principles and operation of devices, kits and corresponding methods according to the present invention may be better understood with reference to the drawings and the accompanying description.

Figure 1A:
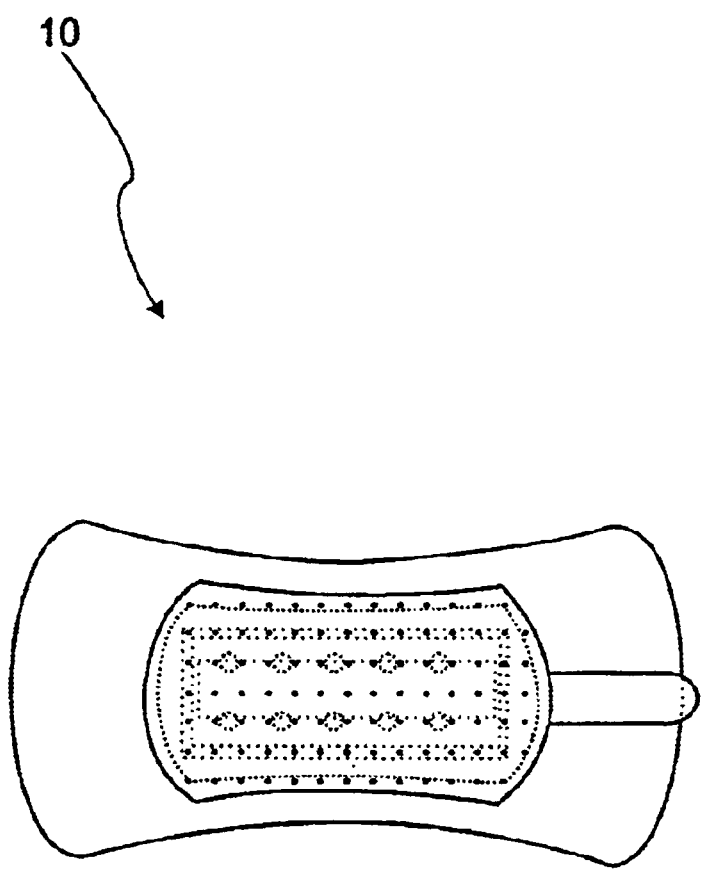
FIG. 1A is a plan view of an absorbent pad from a kit for obtaining a biological sample, constructed and operative according to the teachings of the present invention.
Figure 1B:
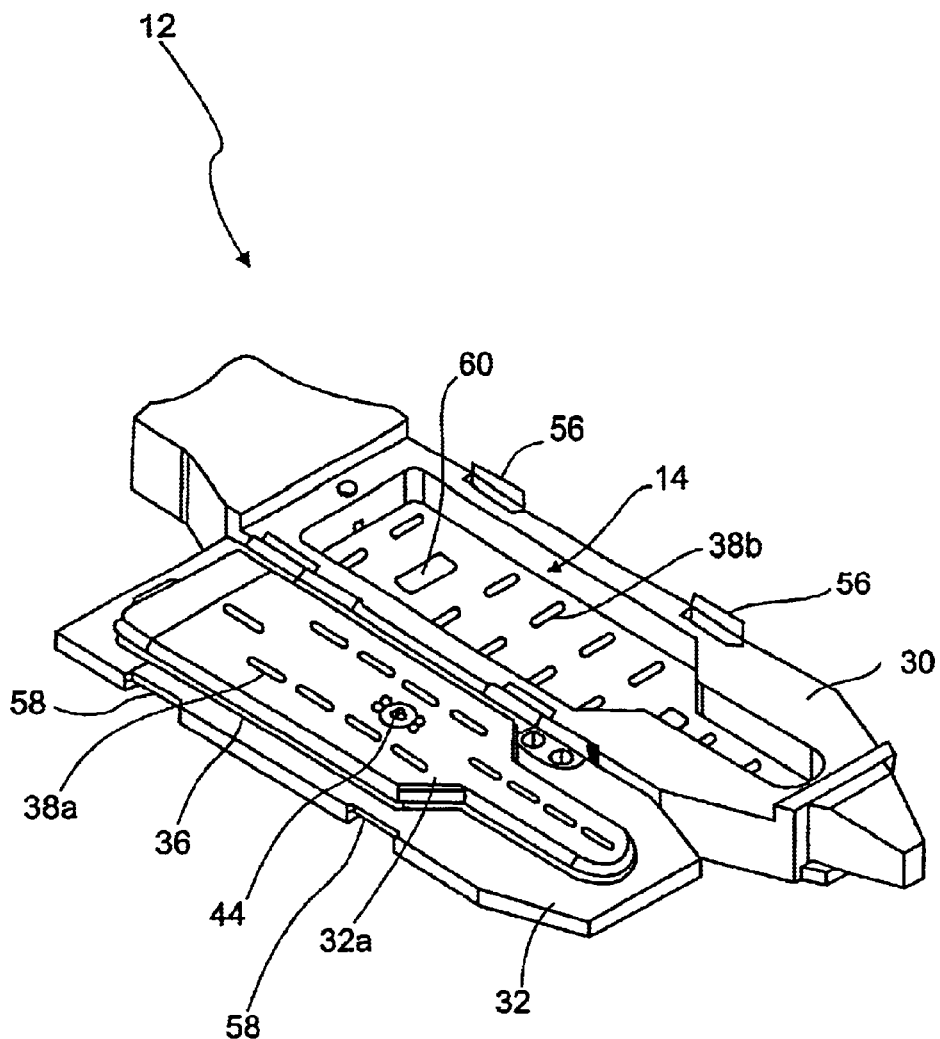
FIG. 1B is an isometric view of a portable device from a kit for obtaining a biological sample, constructed and operative according to the teachings of the present invention.

Referring now to the drawings, FIGS. 1A and 1B show components of a kit, constructed and operative according to the teachings of the present invention, for generating a biological sample from a discharge emitted from a portion of a body. The kit is made up of an absorbent pad 10 for deploying adjacent to the portion of the body, and a portable device 12.

Generally speaking, use of the kit, corresponding to the method of the present invention, is as follows. Absorbent pad 10 is deployed adjacent to the portion of the body for a period of time, so as to allow it to absorb a discharge. At least a part of absorbent pad 10 is then inserted into a sample chamber 14 of portable device 12, a quantity of sample extraction solution is added and sample chamber 14 is sealed. Once sealed, portable device 12 is conveniently transportable to a remote location for processing of the biological sample dissolved within the sample extraction solution.

It will readily be appreciated that the present invention provides a highly advantageous system and method for obtaining a biological sample. Since the sample is collected by an absorbent pad, the invention provides all the advantages of home sampling without the costs, inconvenience and/or embarrassment of an extra visit to a healthcare professional for sampling. At the same time, by sealing the sample soon after collection together with a suitably designed extraction solution, the diagnostic value of the sample can be reliably maintained or even enhanced during the period until the sample reaches analytic facilities for processing. These and other advantages of the present invention will become clearer from the following description.

It should be noted that the present invention is useful in a wide range of applications in which diagnostic or other tests are to be performed upon a bodily discharge. By way of a non-limiting but preferred example, the invention will be described in the context of sampling vaginal secretions. It will be self-evident to one ordinarily skilled in the art that the invention may readily be applied also to pads, bandages, diapers and other absorbent elements for generating biological samples from regular or irregular bodily discharges of substantially any type, and for use in substantially any test.

Turning now to the features of the kit, and the corresponding method steps, of the present invention in more detail, pad 10 will now be described more fully with reference to FIGS. 1A, 2 and 3. The features of portable device 12 will be described more fully below with reference to FIGS. 1B and 4–11, and two alternative implementations of the portable device will be described briefly thereafter with reference to FIGS. 12–14. It should be noted that, both the pad and the portable device are believed to include a number of patentable features when considered individually, in addition to the patentable combination of the kit as a whole. These features will be evident to one ordinarily skilled in the art from the following description.

Figure 2:
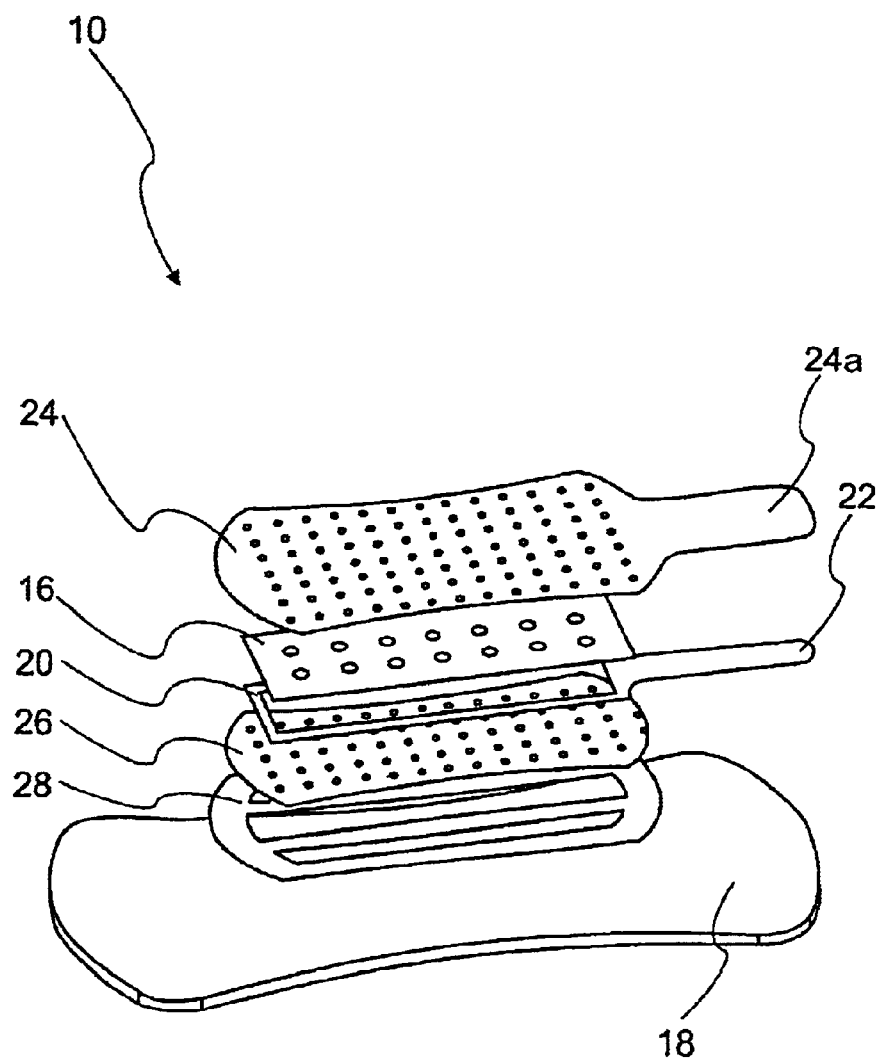
FIG. 2 is an exploded isometric view of the pad of FIG. 1A.
Figure 3:
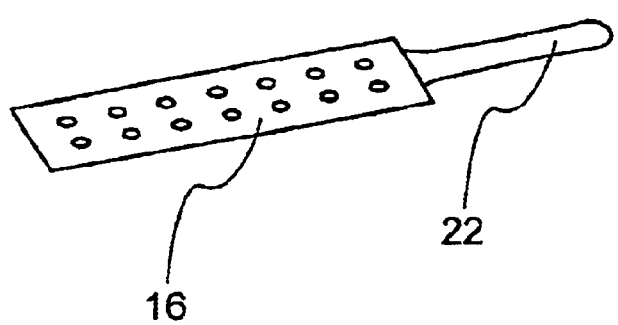
FIG. 3 is an isometric view of a sampling membrane and accompanying support structure after withdrawal from the pad of FIG. 1A.
Figure 4:
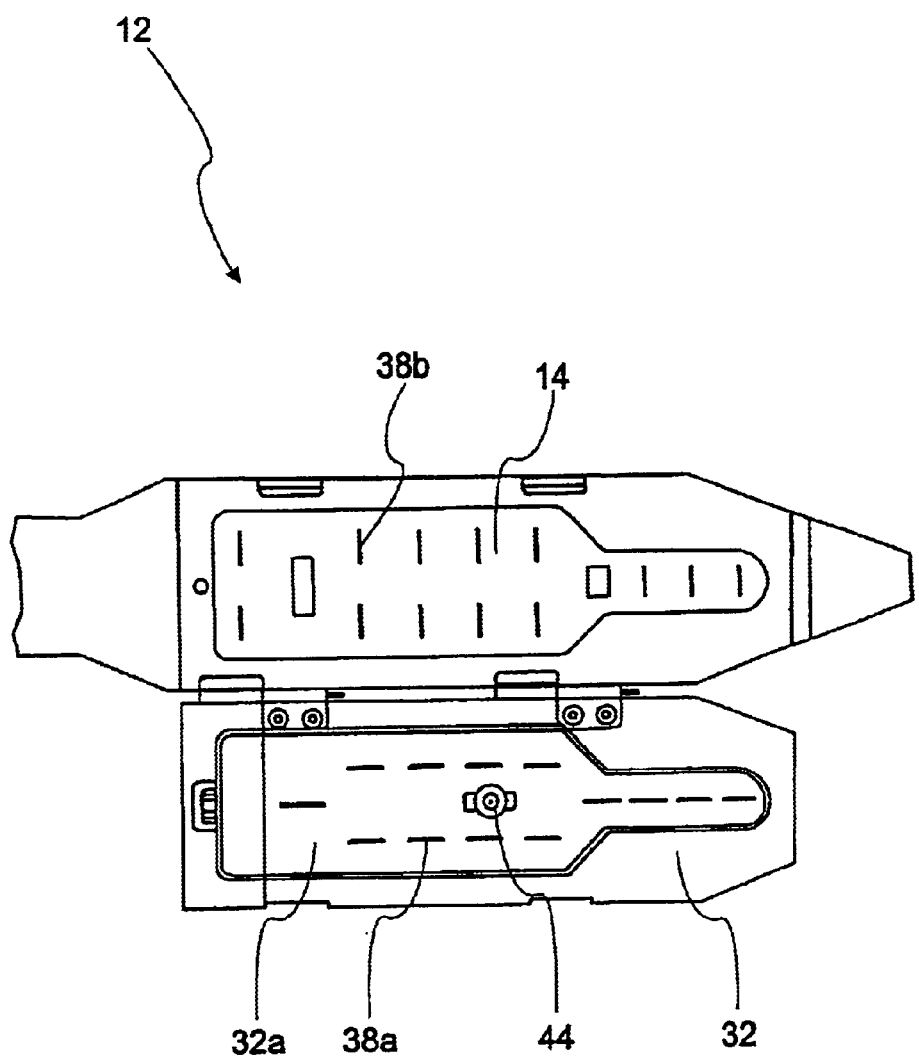
FIG. 4 is a top view of the portable device of FIG. 1B in an open state.

FIG. 2 shows an exploded view of pad 10 according to one preferred implementation. In order to facilitate efficient transfer of the biological sample to a relatively small quantity of solution, pad 10 preferably includes a sampling membrane 16 configured to retain at least one biological material. Preferably, the sampling membrane is configured to bind proteins, thereby attracting and retaining a wide range of pathogens. Membranes with such properties are well known in the art, and are commercially available. One non-limiting example of a suitable membrane is commercially available under the brandname "Nitran N-plus" from S. & S.

The membrane is advantageously deployed at or near the face of the pad positioned proximal to the body, thereby maximizing sample collection prior to absorption into the absorbent layer 18 of pad 10. The membrane is chosen to be porous, either inherently or through provision of perforations, so as to allow fluids to pass through to the absorbent material.

In order to facilitate removal of sampling membrane 16, pad 10 preferably also includes a frame 20 to which the membrane 16 is mounted. Frame 20 is configured to be withdrawn from absorbent pad 10, typically by use of a handle 22. Handle 22 may be implemented as a simple draw-string, or as a handle integrally formed with frame 20 as shown here. FIG. 3 shows sampling membrane 16 attached to frame 20 with integral handle 22 as it appears after removal from pad 10.

Membrane 16 is typically sandwiched between protective layers 24 and 26. An example of suitable material is micro-perforated polyethylene film. The outward-facing layer 24 may optionally have an extension 24a to overlie part or all of handle 22 so as to protect from rubbing against the skin. The entire membrane assembly is typically attached to the absorbent layer 18 by two-sided adhesive tape 28. Pad 10 is typically manufactured as a single unit ready for use. Alternatively, the membrane assembly may optionally be supplied as an adhesive label for attachment by the patient to convert a conventional absorbent pad.

The use of a sampling membrane which, in itself, has minimal fluid retention to accumulate the biological sample has major advantages and particular synergy in the context of the present invention. Specifically, the use of such a membrane facilitates the extraction of the sample into a particularly small quantity of solution, as will be described below in more detail.

Turning now to the features of portable device 12 in more detail, this includes a housing having a base portion 30 formed with a sample chamber 14 for receiving the sampling membrane 16, and a lid portion 32 configured for sealingly closing sample chamber 14.

It is envisaged that the aforementioned sample extraction solution may be supplied in a container separate from portable device 12, and such implementations are considered to fall within a broad interpretation of the present invention. More preferably, however, portable device 12 includes a receptacle within which the sample extraction solution is stored prior to adding into the sample chamber. In the particularly preferred implementation illustrated here, the receptacle is an injector device 34 associated with the housing, typically as part of lid portion 32, and pre-charged with a quantity of sample extracting solution. This injector device 34 may advantageously be configured to be activated by closing of lid portion 32 to inject at least part of the quantity of sample extracting solution into sample chamber 14. Details of one particular implementation of this feature will be discussed further below with reference to FIGS. 6–8.

As mentioned earlier, the extraction of a biological sample from an unknown position on a pad presents a number of technical problems. Specifically, in order to achieve a sufficient concentration of the sample, a total volume of not more than a few cc's of solution should be used. Such a small volume is not generally sufficient for extraction of a sample from the full area of a pad, typically in excess of 20 cm$^2$.

To address this problem, sample chamber 14 is preferably configured as a "flat" chamber, meaning that one dimension ("depth") is at least an order of magnitude less than its other two dimensions ("length" and "breadth"). Thus, in this example, sample chamber 14 is configured to have an open area of at least about 20 cm$^2$, allowing for insertion of the sampling membrane 16 as a flat sheet without folding. At the same time, lid portion 32 is formed with a projecting area 32a which complements the recess within base portion 30 to reduce the total enclosed volume of sample chamber 14 when sealed to no more than about 5 cc, and preferably between 1.5 and 3 cc. A resilient sealing element 36, typically formed from silicone rubber, preferably circumscribes projecting area 32a to ensure an effective seal when lid portion 32 is closed.

The upper surface of sample chamber 14 provided by projecting area 32a and the facing lower surface provided by base portion 30 are preferably both formed with a plurality of projections 38a, 38b projecting into the enclosed volume of chamber 14. These projections serve to suspend sampling membrane 16 away from the surfaces of the sample chamber, thereby ensuring effective access of the sample extracting solution to all parts of the membrane. Most preferably, opposing projections 38a, 38h are implemented as nonparallel elongated projections such that the projections grip the membrane at a number of highly localized points of intersection. This reduces obstruction of fluid flow around the membrane to a minimum.

Lid portion 32 is preferably hingedly attached to base portion 30. Where device 12 is formed primarily from molded polymer material, base portion 30 and lid portion 32 may most conveniently be integrally molded with an integral hinge interconnecting them, as is known in the art of plastic injection molding.

The provision of projection area 32a of lid portion 32 gives the middle region of lid portion 32 a significant depth. This depth is preferably used to provide a recessed portion which at least partially accommodates the volume of injector device 34 as may be seen, for example, in FIGS. 9A–9C. A preferred structure of injector device 34 can also be seen in these figures. Specifically, injector device 34 is here formed as a syringe with a spring-loaded piston 40 biased by a compression spring 42 to inject the pre-loaded solution through a laterally-placed, pressure-differential-actuated elastomeric valve 44 (also visible in FIGS. 1B and 4).

As mentioned earlier, it is a particular preferred feature of certain implementations of the present invention that injector device 34 is automatically actuated on closing of lid portion 32 to introduce the sample extraction solution into sample chamber 14. This greatly simplifies use of the kit, avoiding the need for any "laboratory-type" non-user-friendly steps of adding reagents. Instead, use of the kit involves straightforward intuitive steps such as removing membrane 16 from pad 10, inserting it into chamber 14, and closing the lid. One non-limiting example of a preferred mechanism for performing the automatic injection will now be described with reference to FIGS. 6–8.

Figure 6:
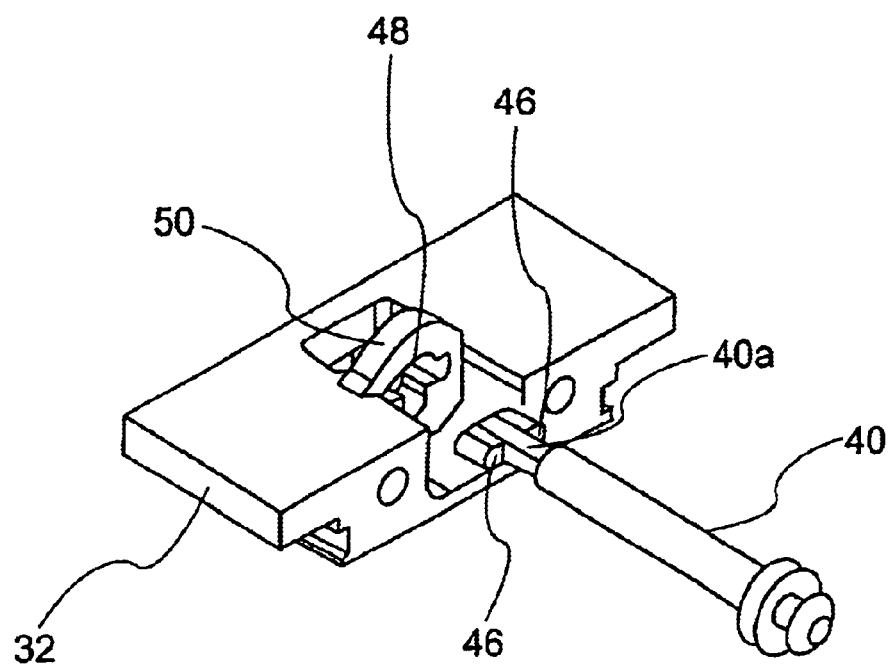
FIG. 6 is an enlarged isometric view of a piston and associated catch element from the portable device of FIG. 1B.

Specifically, FIG. 6 shows a preferred form of piston 40 which has a rear portion 40a with lateral projections 46. Rear portion 40a is initially engaged within a keyhole-type slot 48 formed in a catch element 50 which is mounted in a recess of lid portion 32. The term "keyhole-type slot" is used herein to refer to a slot in which a lateral dimension of a first portion of the slot is greater than the lateral dimension of a second portion of the slot, in a manner similar to a conventional keyhole shape. Clearly, the slot thus defined may differ significantly from the conventional keyhole shape, as exemplified by slot 48 illustrated here.

Figure 7:
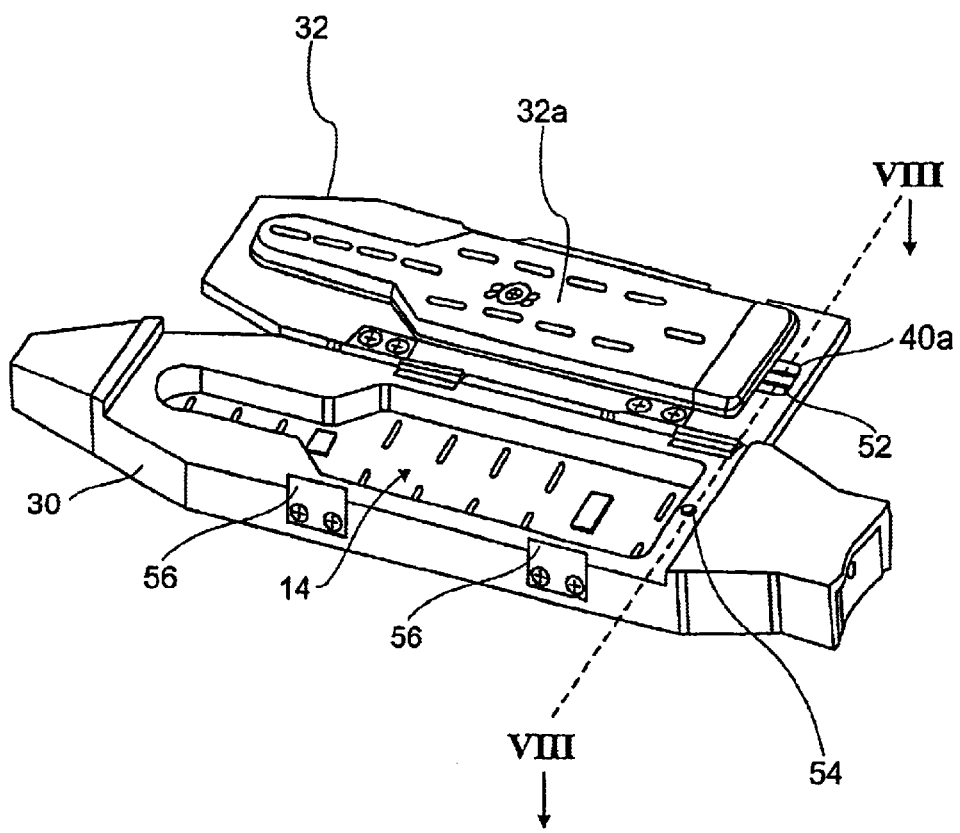
FIG. 7 is an additional isometric view of the portable device of FIG. 1B in an open state better illustrating features for automatically releasing the catch of FIG. 6.

Turning now to FIG. 7, in order to achieve automatic actuation of injector device 34, rear portion 40a of piston 40 is preferably initially positioned so as to extend beyond the end of sample chamber 14. This allows an opening 52 to be formed through a flange of lid portion 32 so as to expose the underside of rear portion 40a. The upwardly-facing surface of base portion 30 opposite opening 52 is provided with a corresponding projection or pin 54.

Figure 8A:
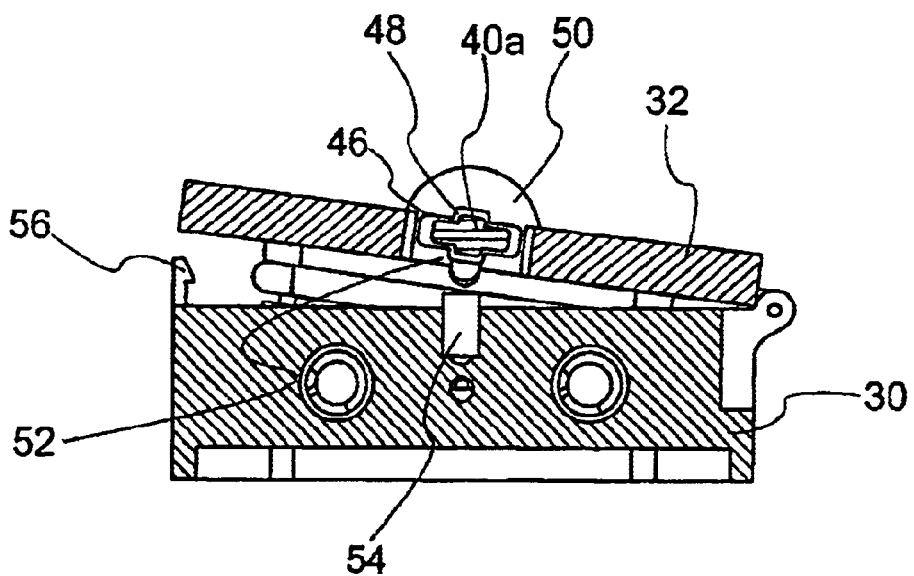
FIGS. 8A, 8B and 8C are cross-sectional views taken as indicated by the dashed line VIII—VIII in FIG. 7 showing a sequence of positions immediately prior to and after closing of the portable device of FIG. 1B.
Figure 8B:
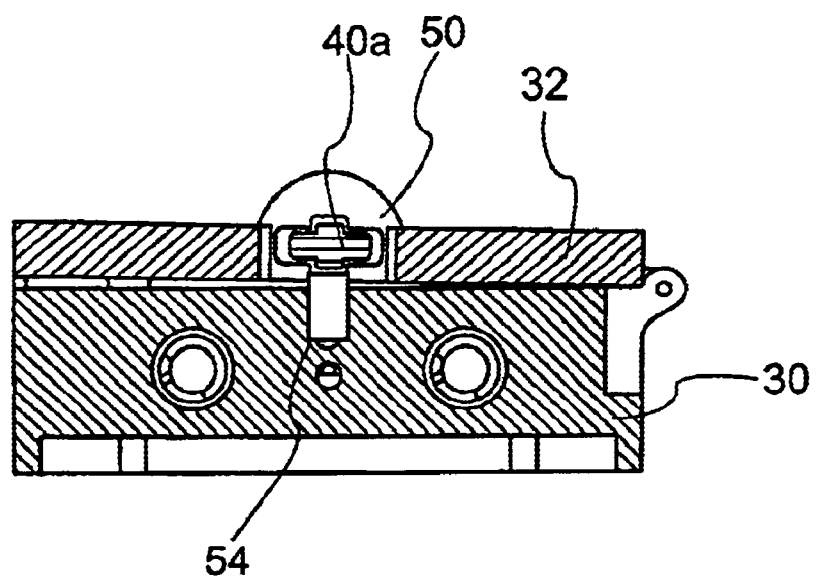
Figure 8C:
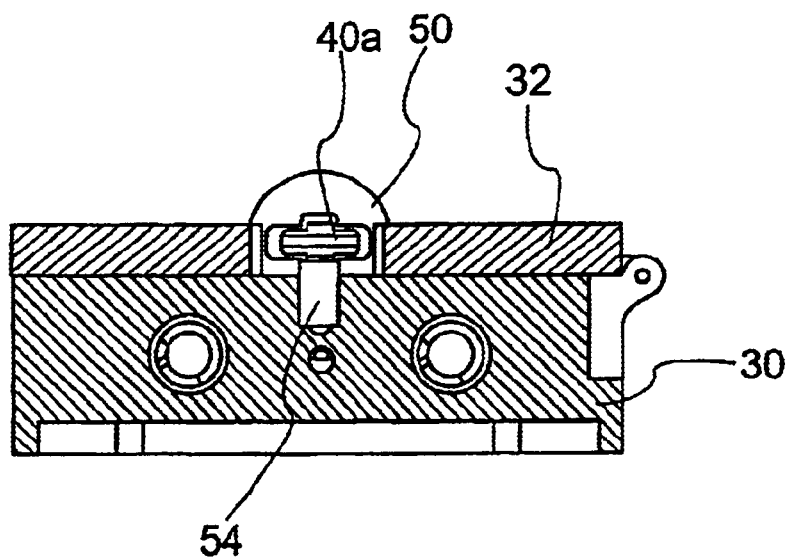

FIGS. 8A–8C show the interaction of these elements as lid portion 32 is closed. Prior to closing (FIG. 8A), rear portion 40a is locked in its retracted position by lateral projections 46 which are lodged against the edges of slot 48. As lid portion 32 is closed, rear portion 40a first comes into contact with pin 54 (FIG. 8B) and then, substantially contemporaneously with full closure of lid portion 32, moves sufficiently relative to slot 48 for projections 46 to clear the edges of the slot (FIG. 8C). Piston 40 is then free to move under the action of pre-loaded spring 42 from the position of FIG. 9A to that of FIG. 9B, thereby injecting the sample extraction solution into sample chamber 14. This typically results in a somewhat elevated pressure within chamber 14, preferably falling in the range of 1.5 to 2.5 atmospheres.

Referring back to FIG. 6, the use of bilateral projections 46, i.e., two lateral projections on opposite sides of rear portion 40a, is particularly advantageous since it provides the possibility of locking piston 40 against accidental premature release by rotating it through 90° about its longitudinal axis, for example during assembly of the device.

In order to avoid accidental spillage and/or contamination of a sample, portable device 12 preferably also features a snap-lock configuration deployed to lock lid portion 32 closed against the base portion 30. In the example illustrated here, this is achieved by resilient clips 56 along the edge of base portion 30 which engage corresponding recesses 58 along the edge of lid portion 32. This snap-lock configuration is designed to provide positive engagement to ensure effective sealing of sample chamber 14. The configuration is preferably also resistant to manual opening of the device.

As mentioned earlier, the present invention is particularly advantageous in that portable device 12 maintains, or even enhances, sample quality during a period of transportation to the location where analysis is to be performed. To this end, the composition of the sample extraction solution should be suitably chosen according to the type of test to be performed, in a manner well within the capabilities of one ordinarily skilled in the art.

In various preferred implementations, at least one sample pre-processing agent is deployed so as to be mixed within sample chamber 14. The term "pre-processing agent" is used in this context to refer to any material which is effective to enhance sample quality, or to prevent an effect which might otherwise adversely affect the quality of the sample. Preferably, the preprocessing agent includes at least one nutrient (e.g., vitamins or polysaccharides) for maintaining activity of a pathogen and/or at least one antibiotic agent for preventing development of certain bacteria which could otherwise overrun the specimen.

Optionally, the sample pre-processing agent(s) may be provided in solution as part of the sample extraction solution. More preferably, the preprocessing agent(s) are provided as a dry material, illustrated here as "tablets" 60, deployed on an inward facing surface such as the bottom surface of sample chamber 14. The material then dissolves and mixes in the sample extraction solution released after closure of the device. The use of dry materials provides a greatly increased shelf-life for reagents of these kinds.

As a further option for enhancing sample quality, portable device 12 may be supplemented by a disposable heating or cooling device (not shown) deployed to maintain the biological sample at a temperature above or below the ambient temperature for a given time period. Thus, by way of example, a small electric heating unit or a unit with a slow exothermic chemical reaction may be used to maintain the sample at around 29° C. which is considered optimal for enhancing a candida sample. Similarly, a cooling unit, based for example on controlled release of gas pressure, may be used to ensure that the temperature of a chlamydia sample does not exceed about 24° C. on a hot day.

It should also be noted that the transportation of the sample in itself performs a useful role according to the present invention. Specifically, motion of portable device 12 serves to mix the sample extraction solution around within chamber 14, thereby contributing to the effective extraction of the biological sample.

In a basic implementation of the present invention, portable device 12 may be punctured or cut open in order to access the sample for testing. In more preferred implementations, portable device 12 is further provided with a manually operable dispensing mechanism configured for dispensing a controlled quantity of liquid from sample chamber 14. Although the dispensing mechanism may optionally be implemented by further modification of the injector device 34 described above, a separate implementation of the dispensing mechanism is currently preferred.

Figure 9A:
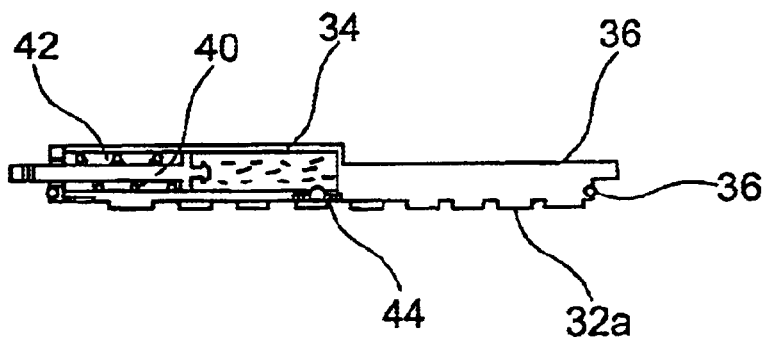
FIG. 9A is a cross-sectional view taken through a lid portion of the portable device of FIG. 1B prior to closing.
Figure 9B:
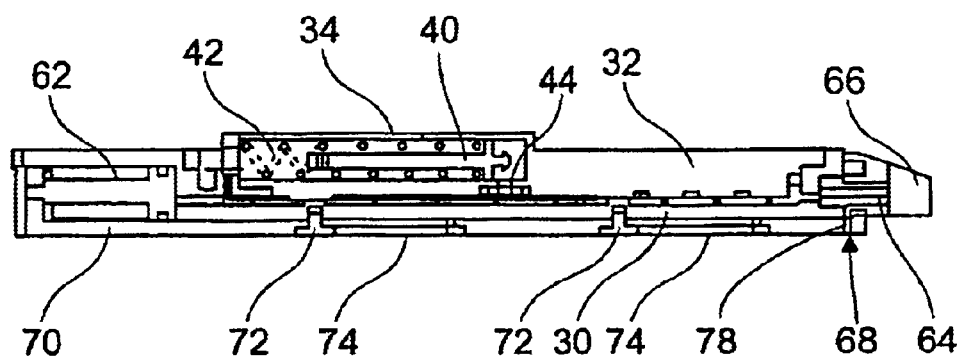
FIG. 9B is a cross-sectional view taken through the portable device of FIG. 1B after closing.
Figure 9C:
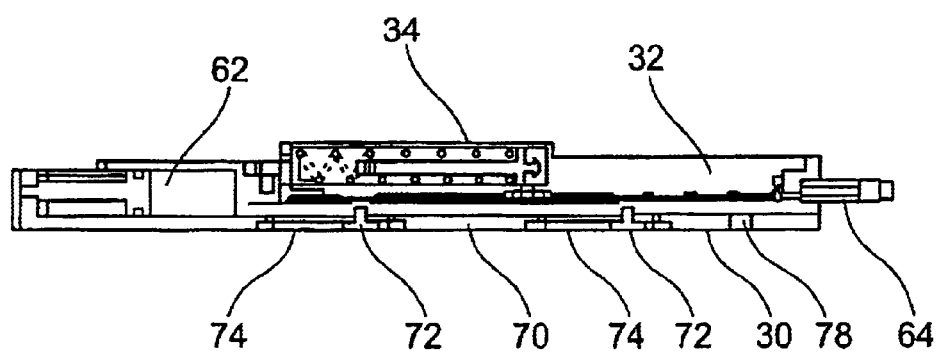
FIG. 9C is a cross-sectional view taken through the portable device of FIG. 1B ready for dispensing a biological sample.
Figure 10:
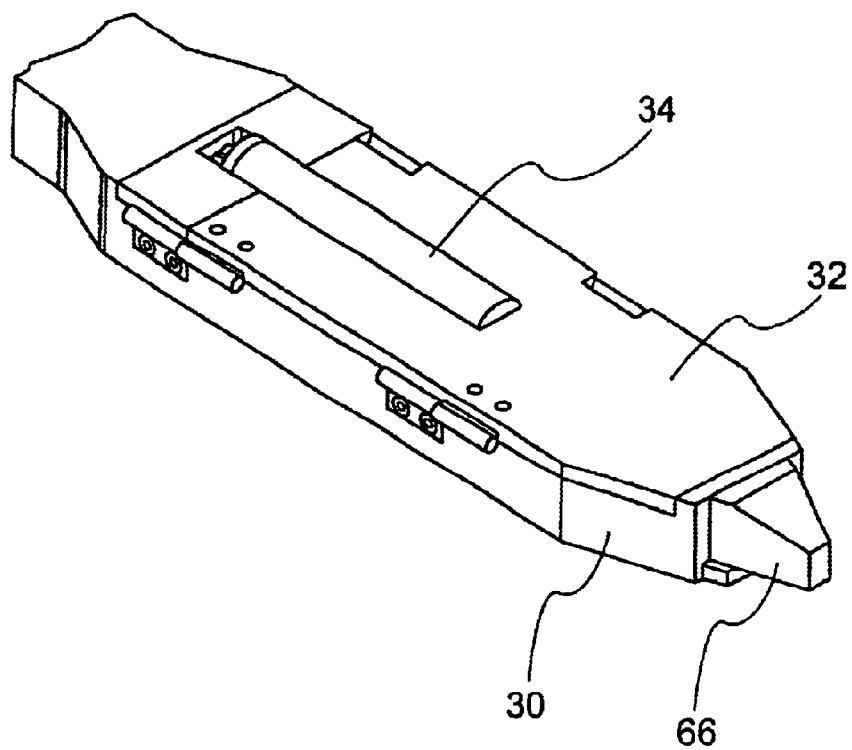
FIG. 10 is an isometric view of the portable device of FIG. 1B after closing.
Figure 11:
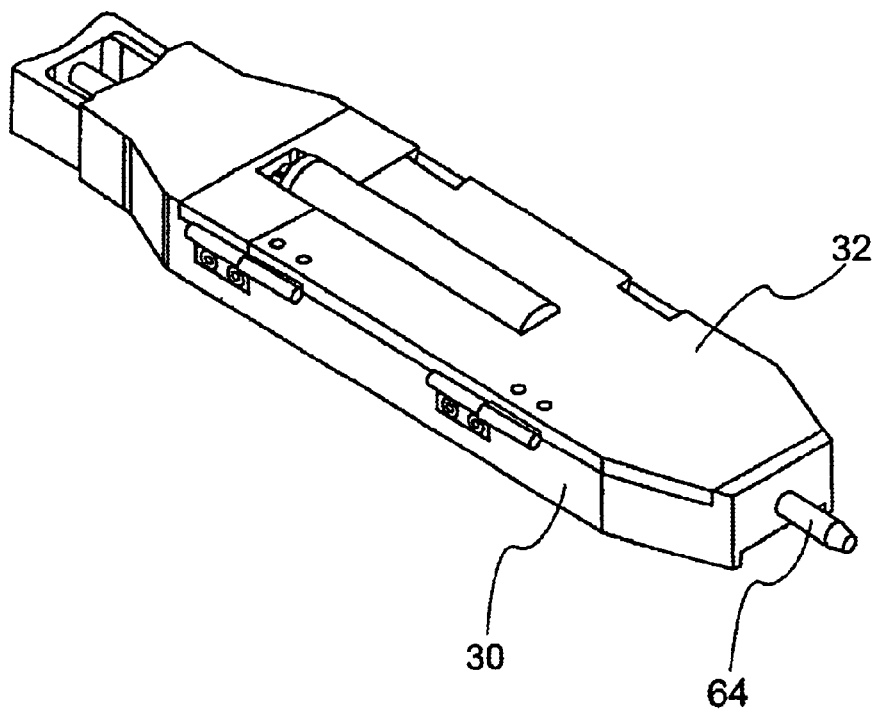
FIG. 11 is an isometric view of the portable device of FIG. 1B ready for dispensing a biological sample.

A preferred example of a manually operable dispensing mechanism is best seen in FIGS. 9B and 9C. Specifically, the dispensing mechanism includes a finger-operable piston mechanism 62 and a dropper aperture 64 in fluid communication with sample chamber 14 for allowing release of liquid droplets from the sample chamber. Dropper aperture 64 is preferably sealed by a removable sealing element 66 until immediately prior to dispensing of liquid from the sample chamber. Most preferably, portable device 12 further includes a lock mechanism 68 configured to selectively prevent operation of the dispensing mechanism. Lock mechanism 68 is preferably mechanically linked to removable sealing element 66 so as to allow operation of the dispensing mechanism when sealing element 66 is removed.

Figure 5:
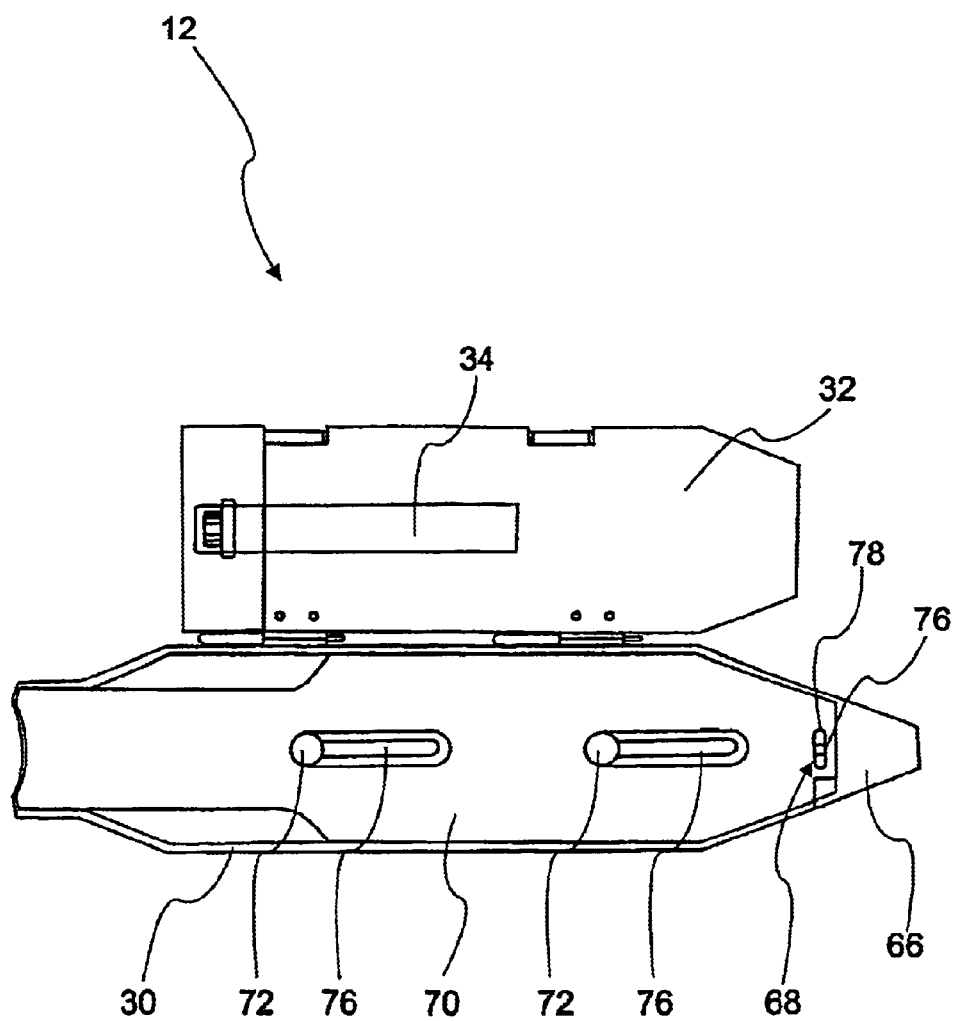
FIG. 5 is a bottom view of the portable device of FIG. 1B in an open state.

The particular implementation of these features illustrated herein will be better understood by referring back momentarily to FIG. 5. Specifically, FIG. 5 shows a slide 70 which is displaceable along portable device 12 along a range of motion defined by bolts 72 engaged within slots 74. At one end of slide 70 is lock mechanism 68, implemented as a pin 76 from sealing element 66 engaged in a channel 78 formed in slide 70. At the other end, slide 70 is linked to piston mechanism 62 such that the piston can only be moved when slide 70 is free. As long a sealing element 66 remains in place, lock mechanism 68 fixes slide 70 so as to prevent operation of the dispensing mechanism. When sealing element 66 is removed by a twisting action, pin 76 clears channel 78 allowing slide 70 and hence piston mechanism 62 to move to an open position (under the action of a spring element not shown), ready for operation by the finger of a lab technician to dispense a controlled quantity of the sample.

Figure 12:
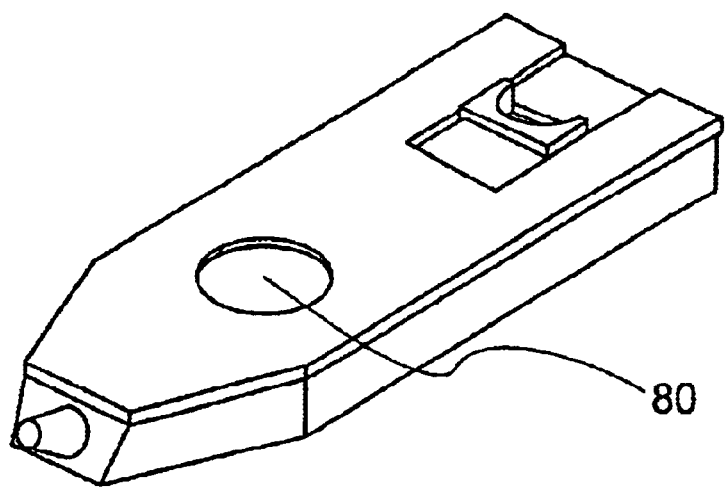
FIG. 12 is an isometric view of an alternative implementation of device of FIG. 1B employing a flexible bulb dispensing mechanism.

Turning now briefly to FIG. 12, this shows an alternative implementation of the portable device of FIG. 1B in which the piston structure of the dispensing mechanism is replaced by a flexible polymeric bulb 80 which may be manually depressed to control dispensing of the sample. In other respects, structure and operation of this implementation is analogous to the implementation described above.

Figure 13:
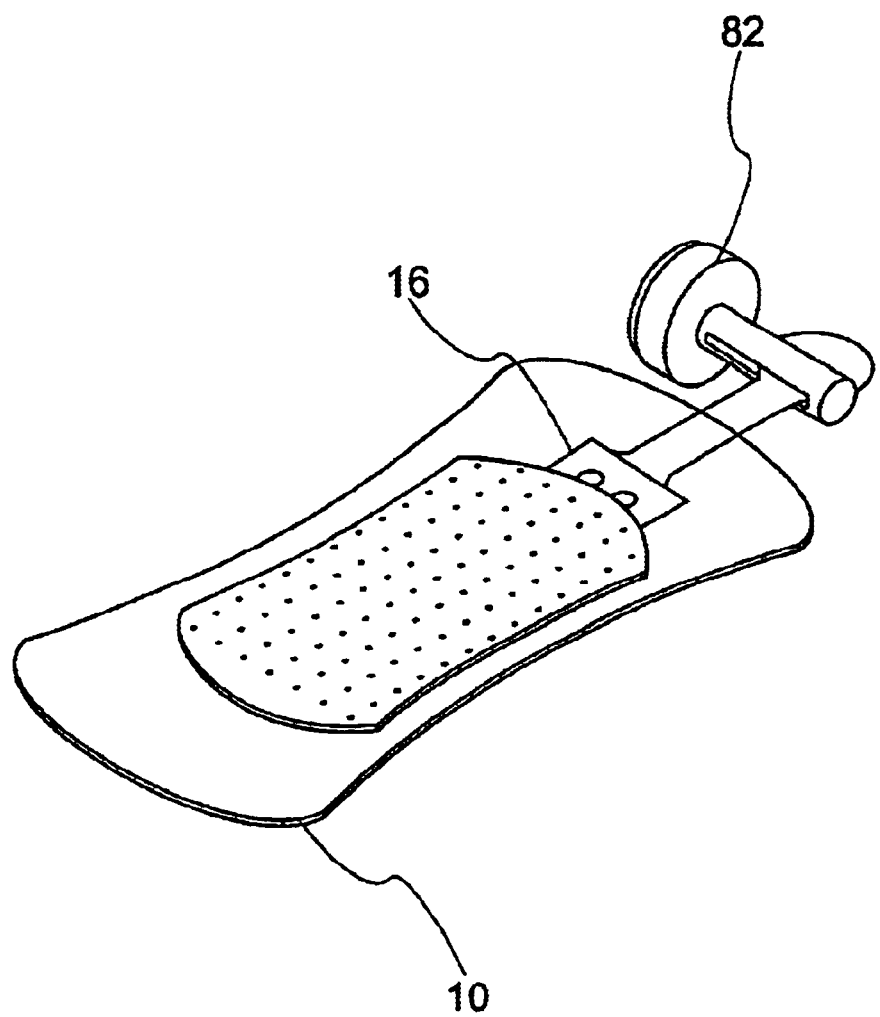
FIG. 13 is an isometric view showing use of a rolling tool for removal of the sampling membrane from the pad of FIG. 1A.
Figure 14:
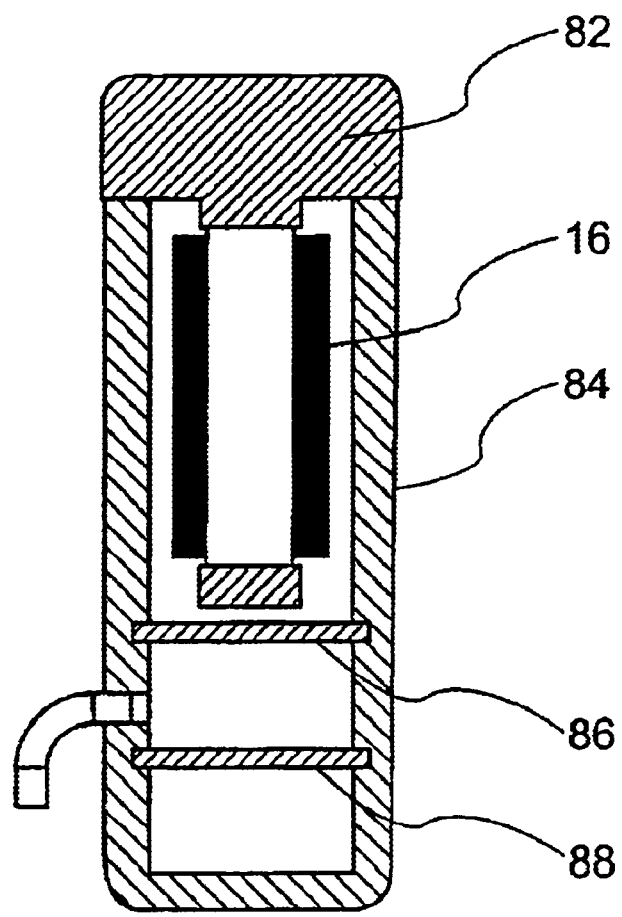
FIG. 14 is a cross-sectional view of a further alternative implementation of the device of FIG. 1B which includes the rolling tool of FIG. 13.

Finally, turning briefly to FIGS. 13 and 14, while the "flat" chamber device configuration described thus far is currently believed to be superior, it should be noted that a number of alternative configurations also fall within the broad scope of the present invention. By way of example, FIG. 13 illustrates the use of a rolling tool 82 to extract membrane 16 from pad 10. This rolling tool then preferably serves as a lid portion of a cylindrical portable device 84 for receiving the rolled membrane 16, as illustrated in FIG. 14. The sample extraction solution may be added manually, may be stored within a flexible pouch which is fractured on insertion of the rolling tool, or may be injected in a manner similar to that described in the earlier implementations.

In certain cases, the total enclosed volume for the cylindrical implementation may lead to over-dilution of the sample. The sample concentration may subsequently be enhanced by use of a pair of filter membranes 86, 88 wherein a first filter membrane blocks particles larger than those of interest while the second retains the pathogens or other particles of interest. The sample is then drawn from the region between the filter membranes.

It will be appreciated that the above descriptions are intended only to serve as examples, and that many other embodiments are possible within the spirit and the scope of the present invention.

What is claimed is:

1. A method for obtaining a biological sample of a discharge emitted from a portion of a body, the method comprising:
   (a) deploying an absorbent pad adjacent to the portion of the body for a period of time;
   (b) inserting at least a part of said absorbent pad into a sample chamber of a portable device, wherein the part of said absorbent pad is a sampling membrane configured to retain at least one biological material;
   (c) adding sample extraction solution into said sample chamber;
   (d) sealing said sample chamber; and
   (e) transporting said portable device to a remote location for processing of the biological sample dissolved within said sample extraction solution.

2. The method of claim 1, wherein said absorbent pad is configured to facilitate removal of the sampling membrane.

3. The method of claim 2, wherein said sampling membrane is associated with a frame located within, and withdrawable from, said absorbent pad.

4. The method of claim 1, wherein said sample chamber is configured to have an open area of at least about 20 cm.sup.2 for insertion of said part of said absorbent pad and an enclosed volume when sealed of no more than about 5 cc.

5. The method of claim 4, wherein said enclosed volume is between 1.5 and 3 cc.

6. The method of claim 1, wherein said portable device further includes a receptacle within which said sample extraction solution is stored prior to adding into said sample chamber.

7. The method of claim 6, wherein said receptacle is implemented as an injector device, and wherein said step of sealing automatically actuates said injector device to perform said step of adding said sample extraction solution into said sample chamber.

8. The method of claim 1, further comprising supplying at least one sample pre-processing agent within said sample chamber.

9. The method of claim 8, wherein said sample pre-processing agent includes at least one nutrient for maintaining activity of a pathogen.

10. The method of claim 8, wherein said sample pre-processing agent includes at least one antibiotic agent.

11. The method of claim 8, wherein said sample pre-processing agent is supplied in a solid form.

12. The method of claim 8, wherein said sample pre-processing agent is supplied within said sample extraction solution.

13. The method of claim 1, further comprising dispensing a quantity of the biological sample dissolved within said sample extraction solution by actuating a dispensing mechanism formed as part of said portable device.

14. The method of claim 1, further comprising actuating a disposable heating device associated with said portable device and deployed to maintain said biological sample at a temperature above ambient temperature for a given time period.

15. The method of claim 1, further comprising actuating a disposable cooling device associated with said portable device and deployed to maintain said biological sample at a temperature below ambient temperature for a given time period.

16. A portable device for use in generating a biological sample from a discharge emitted from a portion of a body onto a sheet of material, the device comprising:
   (a) a housing including:
      (i) abase portion formed with a sample chamber for receiving said sheet of material, and
      (ii) a lid portion configured for sealingly closing said sample chamber, wherein a major part of an enclosed volume of said sample chamber lies between a lower surface provided by the base portion and an upper surface provided by the lid portion, and wherein each of the lower and upper surfaces is formed with a plurality of projections projecting into the enclosed volume; and
   (b) an injector device associated with said housing and pre-charged with a quantity of sample extracting solution, said injector device being configured to be activated by closing of said lid portion to inject at least part of said quantity of sample extracting solution into said sample chamber.

17. The device of claim 16, wherein said sample chamber is configured to have an open area of at least about 20 cm.sup.2 for insertion of said sheet of material.

18. The device of claim 17, wherein said sample chamber is configured to have an enclosed volume when sealed of no more than about 5 cc.

19. The device of claim 17, wherein said sample chamber is configured to have an enclosed volume when sealed of between 1.5 and 3 cc.

20. The device of claim 16, wherein said lid portion is hingedly attached to said base portion.

21. The device of claim 16, wherein said base portion and said lid portion are integrally molded from polymer material, said base portion and said lid portion being interconnected along an integral hinge.

22. The device of claim 16, wherein said lid portion is implemented with a top surface having a recessed portion, said injector device being deployed at least partially within said recessed portion.

23. The device of claim 16, wherein said injector device is implemented as a syringe provided with a spring-loaded piston which is released by closing of said lid portion.

24. The device of claim 16, further comprising a snap-lock configuration deployed to lock said lid portion closed against said base portion.

25. The device of claim 16, further comprising a manually operable dispensing mechanism configured for dispensing a controlled quantity of liquid from said sample chamber.

26. The device of claim 25, wherein said dispensing mechanism includes a finger-operable piston mechanism.

27. The device of claim 26, further comprising a dropper aperture in fluid communication with said sample chamber for allowing release of liquid droplets from said sample chamber.

28. The device of claim 27, further comprising:
   (a) a removable sealing element deployed so as to seal said dropper aperture until immediately prior to dispensing of liquid from said sample chamber; and
   (b) a lock mechanism associated with said dispensing mechanism and configured to selectively prevent operation of said dispensing mechanism, said lock mechanism being mechanically linked to said removable sealing element so as to allow operation of said dispensing mechanism when said sealing element is removed.

29. The device of claim 16, further comprising a quantity of at least one sample pre-processing agent deployed so as to be mixed within said sample chamber.

30. The device of claim 29, wherein said sample pre-processing agent includes at least one nutrient for maintaining activity of a pathogen.

31. The device of claim 29, wherein said sample pre-processing agent includes at least one antibiotic agent.

32. The device of claim 29, wherein said sample pre-processing agent is provided as a dry material deployed on an inward facing surface of said sample chamber.

33. The device of claim 29, wherein said sample pre-processing agent is provided in solution as part of said sample extraction solution.

34. The device of claim 16, further comprising a disposable heating device associated with said housing and selectively actuable to maintain liquid within said sample chamber at a temperature above ambient temperature for a given time period.

35. The method of claim 16, further comprising actuating a disposable cooling device associated with said portable device and deployed to maintain said biological sample at a temperature below ambient temperature for a given time period.

36. A kit for generating a biological sample from a discharge emitted from a portion of a body, the kit comprising:
   (a) an absorbent pad for deploying adjacent to the portion of the body, said pad including a sampling membrane configured to retain at least one biological material, said absorbent pad being configured to facilitate removal of said sampling membrane; and
   (b) a portable device including:
      (i) a housing having:
         (A) a base portion formed with a sample chamber for receiving said sampling membrane, and
         (B) a lid portion configured for sealingly closing said sample chamber; and
      (ii) an injector device associated with said housing and pre-charged with a quantity of sample extracting solution, said injector device being configured to be activated by closing of said lid portion to inject at least part of said quantity of sample extracting solution into said sample chamber.

37. The kit of claim 36, wherein said sampling membrane is configured for binding proteins.

38. The kit of claim 36, wherein said sampling membrane is associated with a frame located within, and withdrawable from, said absorbent pad.

39. The kit of claim 36, wherein said sampling membrane is associated with a handle configured to facilitate withdrawal of said sampling membrane from said absorbent pad.

* * * * *